United States Patent
Moy et al.

(10) Patent No.: US 9,131,907 B2
(45) Date of Patent: Sep. 15, 2015

(54) INTEGRATED PATIENT PULL UP SYSTEM

(75) Inventors: Way I. Moy, Chicago, IL (US); Jeffrey A. Giannini, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 681 days.

(21) Appl. No.: 12/986,383

(22) Filed: Jan. 7, 2011

(65) Prior Publication Data

US 2012/0179289 A1  Jul. 12, 2012

(51) Int. Cl.
 *A61B 6/04* (2006.01)
 *A61B 5/055* (2006.01)
 *A61G 7/10* (2006.01)

(52) U.S. Cl.
 CPC ............. *A61B 6/0457* (2013.01); *A61B 5/0555* (2013.01); *A61B 6/0407* (2013.01); *A61G 7/1015* (2013.01); *A61G 7/1051* (2013.01); *A61G 2200/327* (2013.01); *A61G 2200/34* (2013.01)

(58) Field of Classification Search
 CPC .......... A61B 6/0407; A61B 6/04; A61B 6/44; A61B 6/4405; A61B 6/4429; A61B 6/4452; A61B 6/032; A61B 6/035; A61B 5/0555; A61G 7/1051; A61G 7/1049; A61G 7/1015; A61G 7/1025; A61G 7/10
 USPC ........ 5/83.1, 81.1 R, 85.1, 88.1, 89.1, 81.1 T, 5/81.1 HS, 601, 600; 378/204, 208, 209, 378/20, 193–198
 See application file for complete search history.

(56) References Cited

U.S. PATENT DOCUMENTS

| | | | | |
|---|---|---|---|---|
| 1,630,181 | A * | 5/1927 | Isherwood | 378/194 |
| 2,368,390 | A * | 1/1945 | Winter | 5/86.1 |
| 2,588,124 | A * | 3/1952 | Kizaur | 378/177 |
| 2,659,827 | A * | 11/1953 | Scag et al. | 250/493.1 |
| 2,737,596 | A * | 3/1956 | Haupt et al. | 378/194 |
| 2,835,520 | A * | 5/1958 | Schiring et al. | 403/63 |
| 2,841,717 | A * | 7/1958 | Kizaur | 378/194 |
| 2,876,362 | A * | 3/1959 | Foderaro | 378/194 |
| 2,903,238 | A * | 9/1959 | Flandrick | 254/124 |
| RE24,982 | E * | 5/1961 | Schiring et al. | 403/63 |
| 3,175,085 | A * | 3/1965 | Avery | 378/197 |
| 3,597,774 | A * | 8/1971 | Warren | 5/84.1 |
| 3,750,199 | A * | 8/1973 | Spivey | 5/83.1 |
| 3,902,070 | A * | 8/1975 | Amor et al. | 378/194 |
| 4,019,059 | A * | 4/1977 | Brundin et al. | 378/209 |
| 4,490,833 | A * | 12/1984 | Inomata et al. | 378/58 |
| 4,644,595 | A * | 2/1987 | Daniel | 5/83.1 |
| 4,887,325 | A * | 12/1989 | Tesch | 5/84.1 |
| 4,901,339 | A * | 2/1990 | Heinz et al. | 378/197 |
| 4,944,056 | A * | 7/1990 | Schroeder et al. | 5/85.1 |
| 5,240,218 | A * | 8/1993 | Dye | 248/330.1 |
| 5,579,547 | A * | 12/1996 | Hunt | 5/86.1 |
| 5,694,654 | A * | 12/1997 | Roy | 5/83.1 |
| 6,523,195 | B1 * | 2/2003 | Rodier et al. | 5/83.1 |

(Continued)

*Primary Examiner* — Robert G Santos
(74) *Attorney, Agent, or Firm* — Peter Kendall

(57) ABSTRACT

Systems and a computer-readable medium is provided. In one embodiment, an integrated pull-up system is provided which includes an electric hoist adapted for mounting in one of an upper portion of a medical imaging device, at a base of said medical imaging device, integrated in said medical imaging device, and on a patient handling system ("PHS"). One end of a cable/strap is attached to the hoist. The other end of the cable/strap includes a grab-bar attached thereto. When actuated, the cable/strap retracts and extends to move a patient, holding the grab-bar, towards/from a supine position towards/from a seated position on the PHS.

5 Claims, 6 Drawing Sheets

(56) References Cited

U.S. PATENT DOCUMENTS

| | | | |
|---|---|---|---|
| 6,728,979 B1 * | 5/2004 | Robert | 5/81.1 R |
| 7,240,621 B2 * | 7/2007 | Chepurny et al. | 104/173.1 |
| 7,448,800 B2 * | 11/2008 | Steger et al. | 378/193 |
| 7,458,113 B2 * | 12/2008 | Milam | 5/81.1 HS |
| 7,634,825 B2 * | 12/2009 | Chepurny et al. | 5/83.1 |
| 7,921,484 B2 * | 4/2011 | Bendele et al. | 5/83.1 |
| 8,128,068 B2 * | 3/2012 | Chepurny et al. | 254/358 |
| 8,230,863 B2 * | 7/2012 | Ravikumar et al. | 128/845 |
| 2005/0115914 A1 * | 6/2005 | Chepurny et al. | 212/328 |
| 2006/0071138 A1 * | 4/2006 | Steger et al. | 248/317 |
| 2006/0273292 A1 * | 12/2006 | Milam | 254/343 |
| 2007/0215569 A1 * | 9/2007 | Chepurny et al. | 212/228 |
| 2007/0277815 A1 * | 12/2007 | Ravikumar et al. | 128/99.1 |
| 2008/0201843 A1 * | 8/2008 | Bendele et al. | 5/83.1 |
| 2010/0051889 A1 * | 3/2010 | Chepurny et al. | 254/339 |
| 2012/0179289 A1 * | 7/2012 | Moy et al. | 700/213 |

* cited by examiner

INTEGRATED PATIENT PULL UP SYSTEM

BACKGROUND

1. Field of the Invention

Embodiments herein generally relate to apparatuses for assisting patient movement. In particular, the present invention relates to novel apparatuses for assisting a patient to move to/from a supine position to/from a seated position.

2. Description of the Related Art

Lifts for use in lifting or transporting geriatric and other patients typically lift the patient to/from a bed to/from a chair or testing device. However, when undergoing medical imaging procedures, patients often need assistance when moving to/from a seated position on an imaging bed to/from a supine position on the imaging bed.

Various factors can contribute to the patient needing assistance. For example, patients who are heavy or overweight, weak, and/or injured may not be able to reposition themselves on the imaging bed without assistance, pain, and/or causing further injury. Often, a technologist will try to provide repositioning assistance to the patient. However, there are instances when the technologist does not have sufficient strength to assist the patient, may cause injury to the patient, and/or the patient and/or the technologist does not want to come into contact with each other.

Currently, ceiling mounted and freestanding lift systems are available on the market but often times neither are readily available, are too troublesome to bring in a room, and/or have image quality problems.

Therefore there is a need in the art for an improved patient repositioning assistance.

SUMMARY

These and other deficiencies of the prior art are addressed by embodiments of the present invention, which generally relates to nuclear medicine, and systems for obtaining images of a patient's body organs of interest. In one embodiment, an integrated pull-up system is provided which includes an electric hoist adapted for mounting in one of an upper portion of a medical imaging device, at a base of said medical imaging device, integrated in said medical imaging device, and on a patient handling system ("PHS"). One end of a cable/strap is attached to the hoist. The distant end of the cable/strap includes a grab-bar attached thereto. When actuated, the cable/strap retracts and extends to move a patient, holding the grab-bar, towards/from a supine position towards/from a seated position on the PHS.

According to another embodiment, an integrated pull-up system is provided which includes a gantry and a PHS adapted for passage within the gantry. A boom is coupled to the PHS and includes a cable/strap disposed within the boom. At one end of the boom, an end of the cable/strap is coupled to an electric hoist. At the distant end of the boom, another end of the cable/strap extends outside of the boom.

According to yet another embodiment, a cable/strap is disposed within a boom. One end of the cable/strap extends outside of one end of the boom. A mount is also provided which is adapted to couple another end of the boom to a PHS.

Other embodiments are also provided herein which utilize instructions stored on a computer-readable medium which cause a processor to control a medical imaging system and actuate an electric hoist integrated into the medical imaging system.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of embodiments of the invention. As will be apparent to those skilled in the art, however, various changes using different configurations may be made without departing from the scope of embodiments of the invention. In other instances, well-known features have not been described in order to avoid obscuring embodiments of the invention. Thus, the invention is not considered limited to the particular illustrative embodiments shown in the specification and all such alternate embodiments are intended to be included in the scope of the appended claims.

Embodiments disclosed herein can be used with various medical imaging systems. In addition, although nuclear medical imaging scanners can be manufactured which have the integrated pull-up system built in, nuclear medical imaging scanners can also be retrofitted to include the integrated pull-up system.

Figure 1:
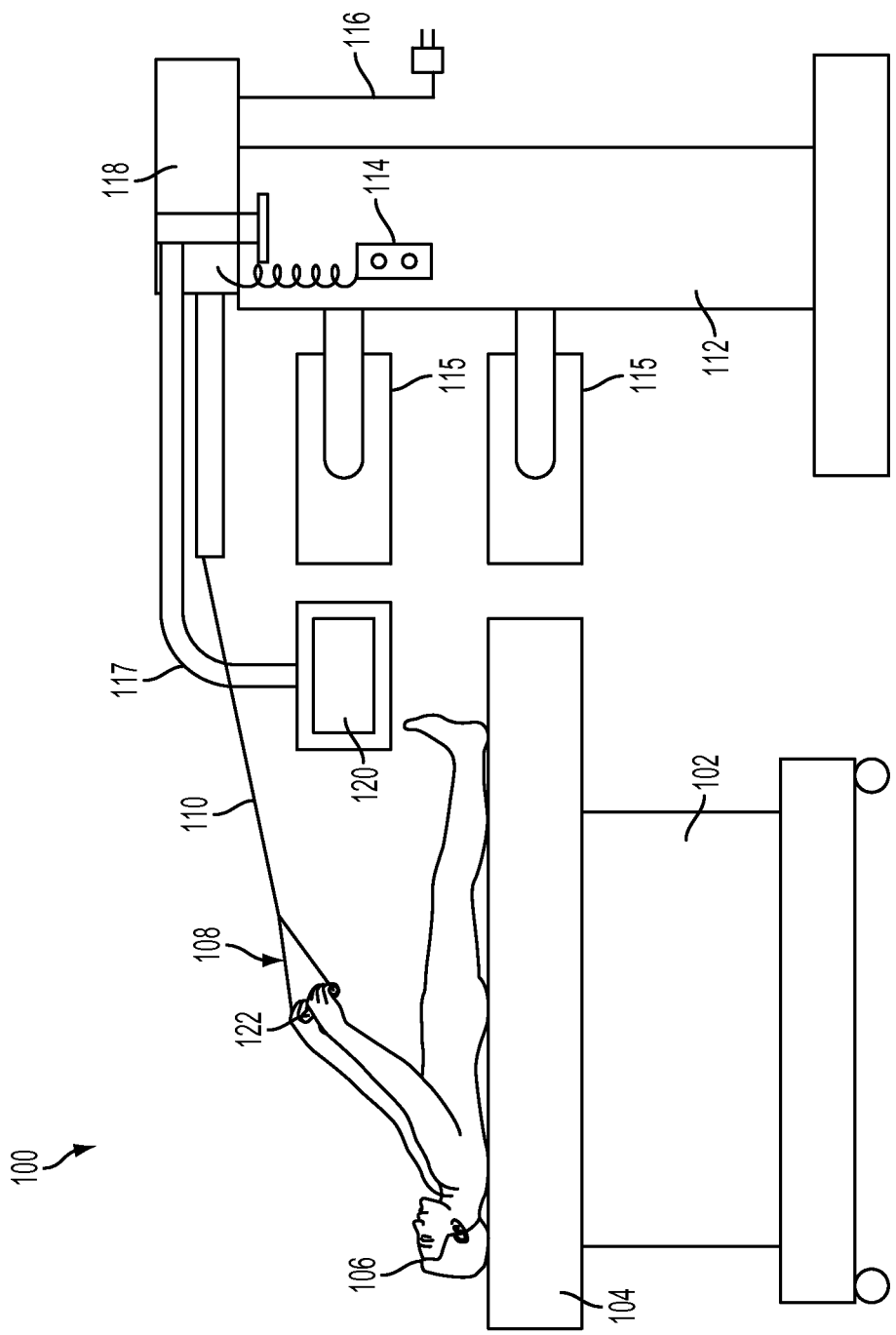
FIG. 1 depicts an embodiment of a first system in accordance with aspects disclosed herein.

FIG. 1 depicts an embodiment of an imaging system 100 in accordance with aspects disclosed herein. FIG. 1 depicts a patient 106 supine on an imaging bed 104. The imaging bed 104 is an upper portion of a patient handling system 102 ("PHS"). The patient 106 is grasping a grab-bar 122. Grab bar 122 may be made of foam, gel, leather, fabric, metal plastic or combinations of the cited materials. The grab-bar 122 is coupled to a handle strap 108. The handle strap is coupled to one end of a cable/strap 110. An opposite end of the cable/strap 110 is coupled to an electric hoist 118. The electric hoist 118 is controlled by a hand controller 114. It should be appreciated by those skilled in the art that in various embodiments the hand controller 114 can also be operated in a detached or remote mode. The electric hoist 118 is depicted as being mounted on top of a gantry 112. The imaging system 100 also includes a patient positioning monitor 120 ("PPM") supported by a PPM boom 117, detectors 115, and power supply cord 116.

A patient who needs assistance to reposition their body holds onto the grab-bar 122. The technologist (not shown) interacts with the hand controller 114 so that the electric hoist 118 either retracts or extends depending upon the needs of the patient. Only one technologist is needed to operate the lift system thereby eliminating a need for multiple people to physically help the ambulatory patient. The integrated pull-up system minimizes the potential for injury for both the technologists and patients, as it would eliminate straining associated with pulling and pushing of the patients.

Positioning the electric hoist 118 on top of the gantry 112, integrated inside of the gantry 112, at the base of the gantry 112, or on the PHS 102 minimizes the overall footprint of the imaging system 100.

Figure 2:
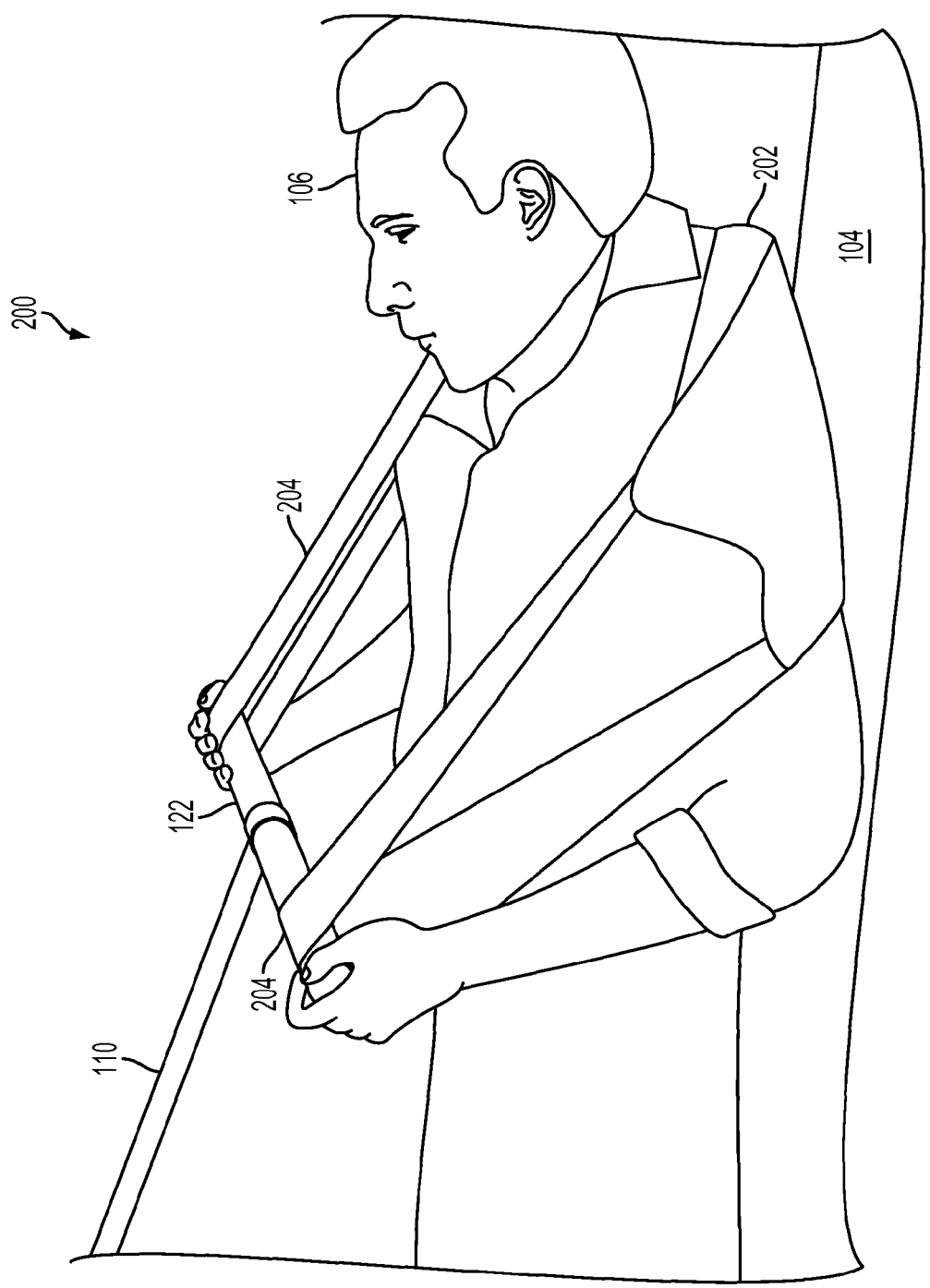
FIG. 2 depicts a first view of a second system in accordance with aspects disclosed herein.
Figure 3:
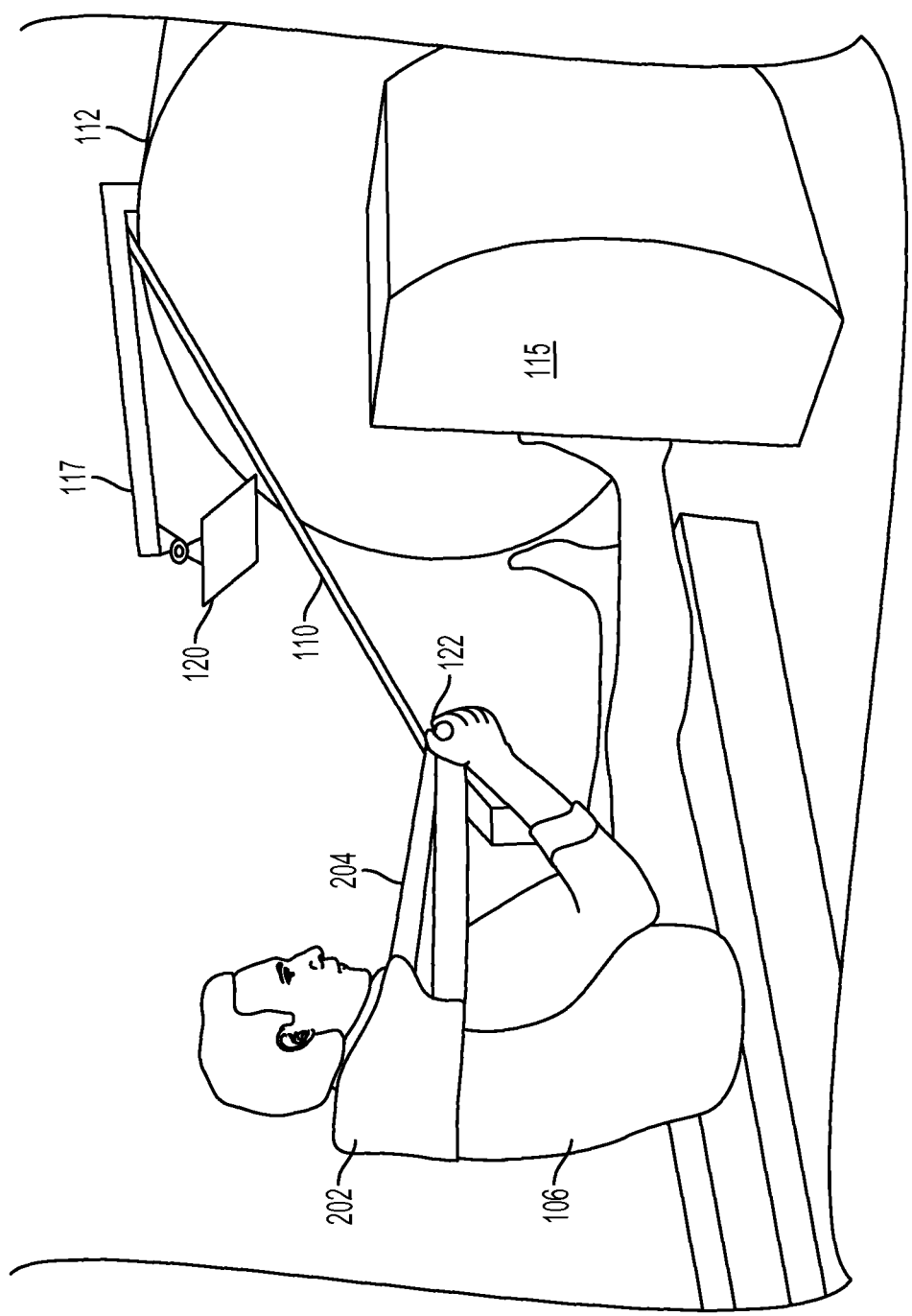
FIG. 3 depicts a second view of the second system in accordance with aspects disclosed herein.

FIG. 2 depicts a first view of a second embodiment of an integrated pull-up system 200 in accordance with aspects disclosed herein. FIG. 2 depicts the patient 106 lying in the supine position. The integrated pull-up system 200 includes the cable/strap 110 coupled to the electric hoist 118 at one end (not shown) and coupled to the grab-bar 122 at the other end. The pull-up system 200 also includes a sling 202. The patient's body is placed inside the sling 202. The sling is coupled to the grab-bar 122 via sling straps 204. The sling 202 may be coupled to the grab-bar 122 by sliding the sling straps 204 onto the grab-bar 122. The sling 202 provides further assistance to patients 106 who do not have sufficient strength to hold onto the grab-bar 122 when the electric hoist 118 retracts or extends the cable/strap 110. For illustrative purposes only, the sling 202 is depicted in FIGS. 2 and 3 as being across the back and shoulders of the patient 106, however those depictions are not intended in any way to limit the scope of the invention. In various embodiments, the sling 202 is positioned under the patient 106 in any manner which supports the upper body of the patient 106 when coupled to the grab-bar 122.

When not in use, the sling straps 204 are removed from the grab-bar 122 and the sling 202 is free to either lay flat on the imaging bed 104 or be removed from contact with the patient 106.

FIG. 3 depicts a second view of the second embodiment of the integrated pull-up system 200 in accordance with aspects disclosed herein. Specifically, FIG. 3 depicts the patient 106 in an upright seated position. As indicated above, the sling 202 provides support to the patient 106 and is coupled to the grab-bar 122 via the sling straps 204.

Although the above embodiments have been described as using a hand control 114 that description is not intended to limit the scope of the invention in any way. For example, the instructions to control the integrated pull-up systems described herein may be incorporated into the controls of the medical imaging device.

Figure 4:
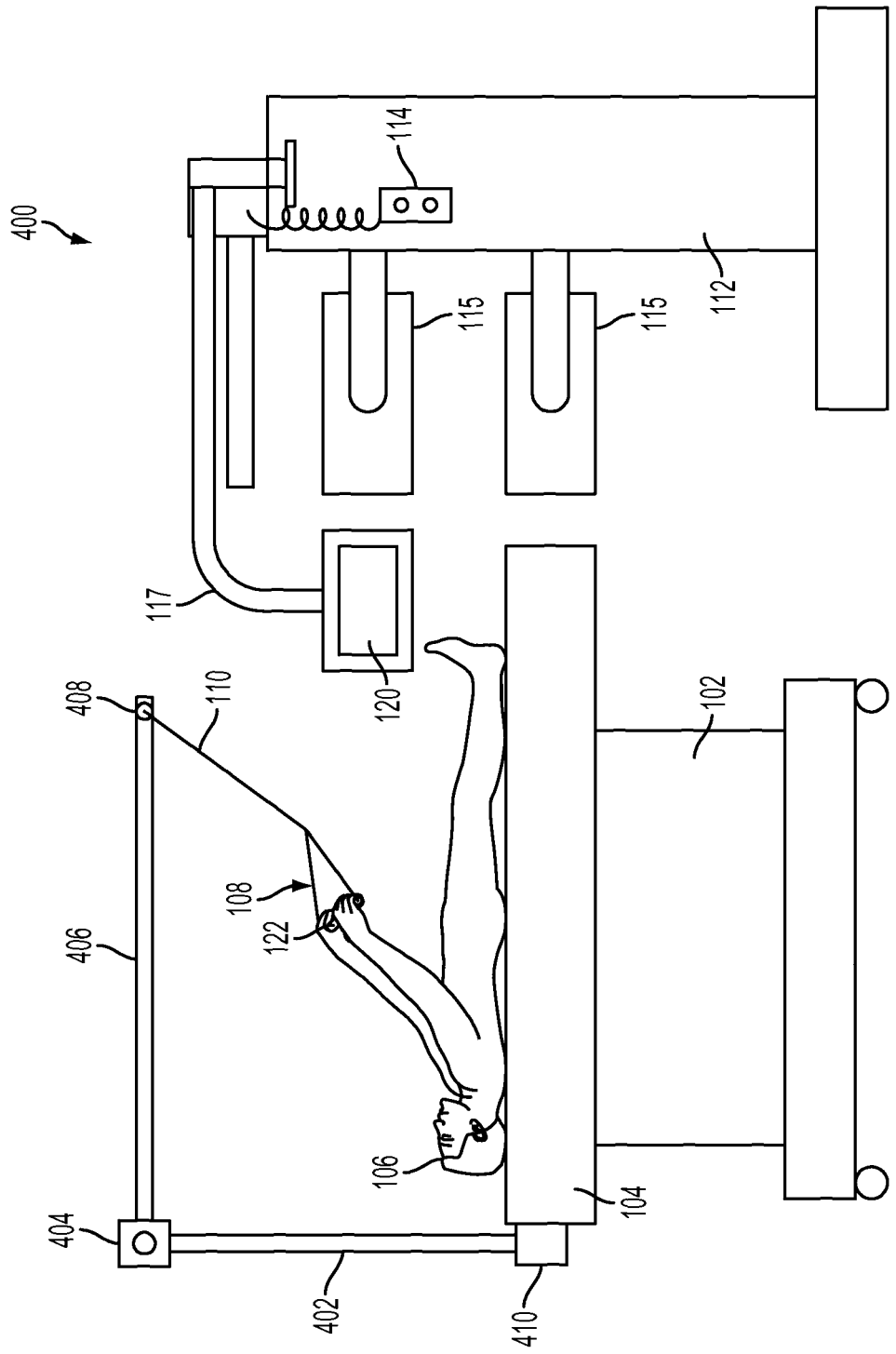
FIG. 4 depicts a side view of a third system in accordance with aspects disclosed herein.
Figure 5:
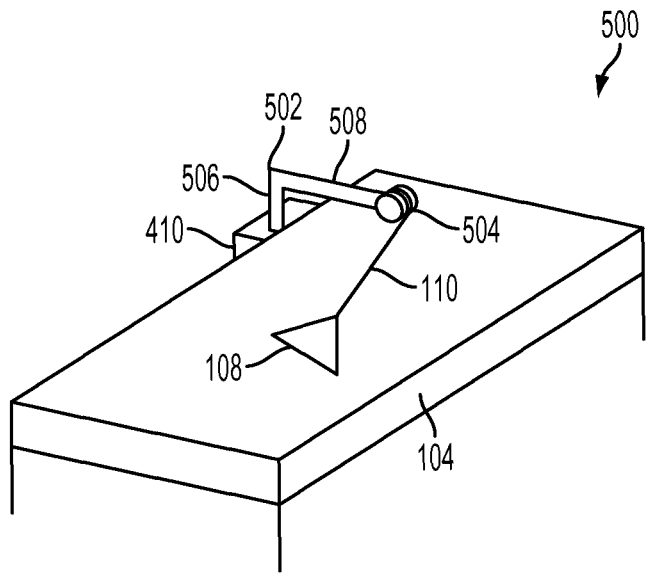
FIG. 5 depicts a side view of a fourth system in accordance with aspects disclosed herein.

In accordance with aspects disclosed herein, it is appreciated that the patient pull-up system may be incorporated into an imaging system in different ways by locating the pull-up system in different regions of the imaging system. For example, FIGS. 4 and 5 depict other locations for integration of the pull-up system into the imaging system. However, those depictions are not intended in any way to limit the scope of the invention or limit where/how the pull-up system is integrated into the imaging system.

FIG. 4 depicts a side view of a third embodiment of an integrated pull-up system 400 in accordance with aspects disclosed herein. Specifically, the system 400 includes the PHS 102, the imaging bed 104, the gantry 112, the hand control 114, and the patient position monitor 120. Each of the aforementioned components operates as described above. The patient pull-up system 400 also includes a mount 410 secured to a distal end (with respect to the gantry 112) of the imaging bed 104. Coupled to the mount 410 is a support pole 402. The support pole 402 extends substantially vertically with respect to the surface of the imaging bed 104. In various embodiments, the height of the support pole 402 is adjustable. At an opposing end of the support pole 402 is a pulley/rotatable member 404. The pulley/rotatable member 404 is also coupled to a boom 406. The boom 406 is substantially horizontal and substantially parallel to the surface (which supports the patient and is in direct contact with the patient) of the imaging bed 104. In various embodiments, the length of the boom 406 is adjustable. In various embodiments, a distal end (with respect to the pulley/rotatable member 404) of the boom 406 includes a pulley 408 therein to allow easier movement of the cable/strap 110 through at least the boom 406 and pulley/rotatable member 404.

When needed, the patient 106 is raised and/or lowered towards/from the substantially seated position towards/from the supine position as indicated above.

FIG. 5 depicts a side view of a fourth system 500 in accordance with aspects disclosed herein. Specifically, the system 500 includes the PHS 102, the imaging bed 104, the gantry 112, the hand control 114, and the patient position monitor 120. Each of the aforementioned components operates as described above. The patient pull-up system 500 also includes a mount 118 secured to a side of the imaging bed 104. Coupled to the mount 118 is a boom 502. A portion 506 of the boom 502 extends substantially vertically, at an end coupled to the mount 118, with respect to a surface (which supports a patient and is in direct contact with the patient) of the imaging bed 104. In various embodiments, the amount of the height extension of the portion 506 is adjustable. A second portion 508 of the boom 502 is substantially horizontal and substantially parallel to the surface (which supports the patient and is in direct contact with the patient) of the imaging bed 104. The opposing portion 508 of the boom 502 also includes a pulley/rotatable member 504. In various embodiments, the length of the second portion 508 of the boom 502 is adjustable.

Although, FIGS. 4 and 5 depict specific locations where the mount 118 is secured to the imaging bed 104, the mount 118 may be secured anywhere on the imaging bed 104 and/or the PHS 102.

It is appreciated that in various embodiments, a motor which facilitates movement (i.e., extension and retraction) of the cable/strap 110 may also be coupled to the PHS 102 and/or imaging bed 104; and in other embodiments, the motor may be coupled to the integrated into the pull-up systems 400 and 500 from other locations.

Although FIGS. 4 and 5 depict the hand control 114 on the gantry 112, in various embodiments, the hand control 114 may be positioned elsewhere in the pull-up systems 400 and 500.

Although not depicted in FIGS. 4 and 5, pull-up systems 400 and 500 may, in various embodiments, include an optional sling 202 and sling straps 204.

Figure 6:
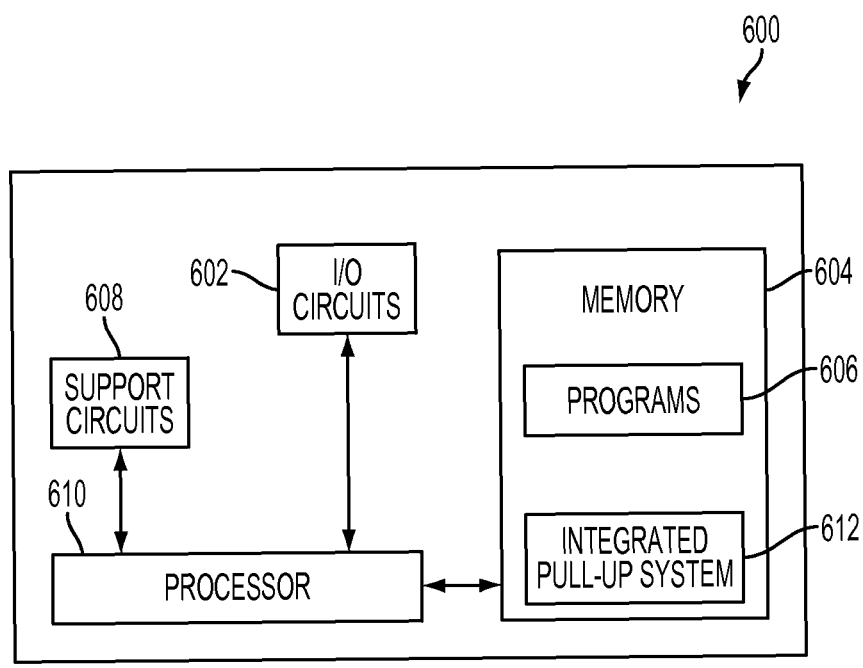
FIG. 6 depicts an embodiment of a high-level block diagram of a computer architecture used in accordance with aspects disclosed herein.

FIG. 6 depicts a high-level block diagram of a general-purpose computer architecture 600 for integrating control of a pull-up system (e.g., pull-up systems 100, 200, 400, and 500) into an imaging system control system. For example, the general-purpose computer 600 is suitable to control a pull-up system (e.g., pull-up systems 100, 200, 400, and 500). The general-purpose computer of FIG. 6 includes a processor 610 as well as a memory 604 for storing control programs and the like. In various embodiments, memory 604 also includes programs (e.g., depicted as a "integrated pull-up system" 612 for controlling retraction and extension of the cable/strap 110) for performing the embodiments described herein. The processor 610 cooperates with conventional support circuitry 608 such as power supplies, clock circuits, cache memory and the like as well as circuits that assist in executing the software routines 606 stored in the memory 604. As such, it is contemplated that some of the process steps discussed herein as software processes may be loaded from a storage device (e.g., an optical drive, floppy drive, disk drive, etc.) and implemented within the memory 604 and operated by the processor 610. Thus, various steps and methods of the present invention can be stored on a computer readable medium. The general-purpose computer 600 also contains input-output circuitry 602 that forms an interface between the various functional elements communicating with the general-purpose computer 600. The pull-up system is in communication (wired communication and/or wireless communication) with the imaging system controller so that the imaging system controller may control the pull-up system.

Although FIG. 6 depicts a general-purpose computer 600 that is programmed to perform various control functions in accordance with the present invention, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. In addition, although one general-purpose computer 600 is depicted, that depiction is for brevity on. It is appreciated that each of the methods described herein can be utilized in separate computers.

Figure 7:
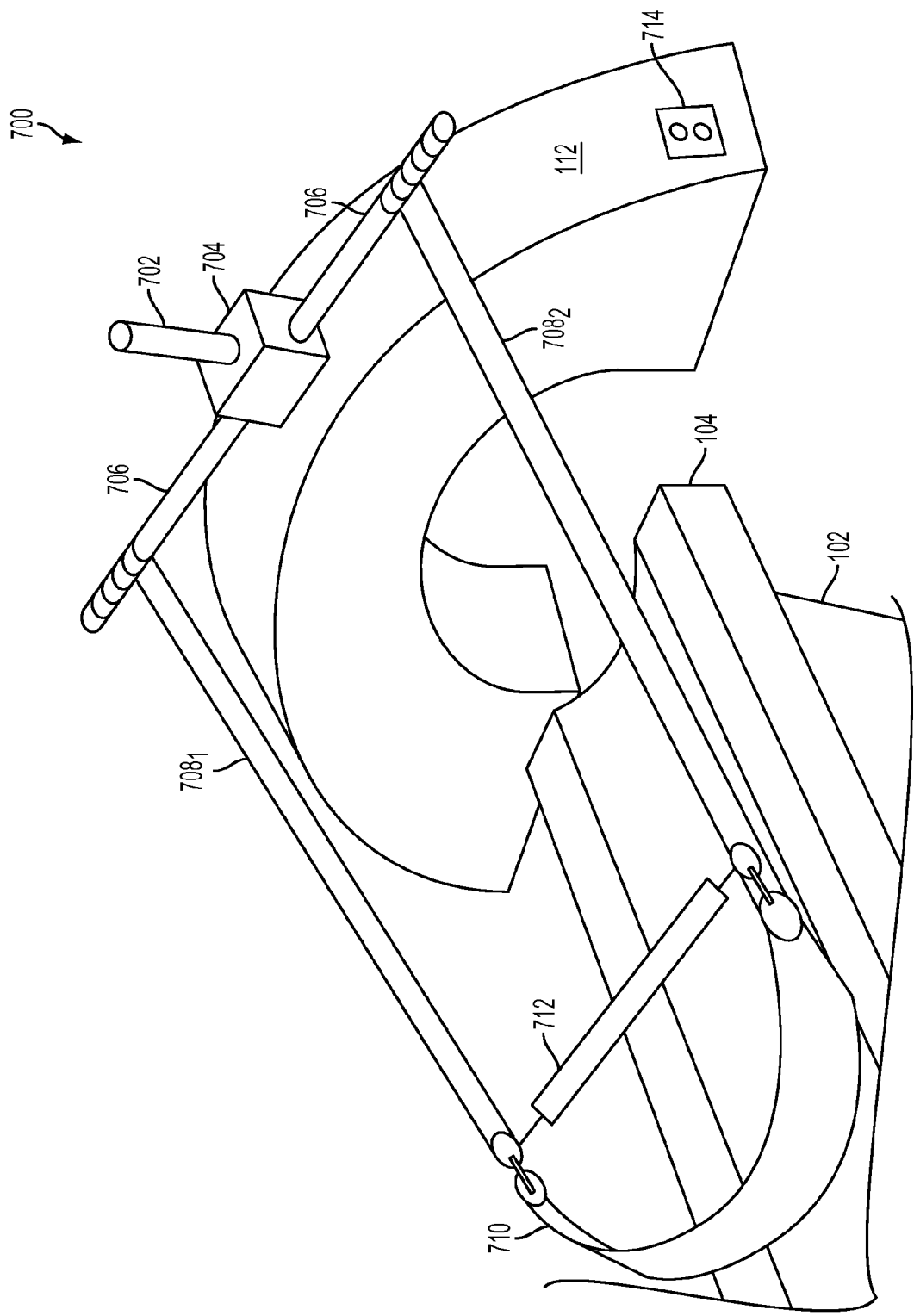
FIG. 7 depicts a side view of a fifth system in accordance with aspects disclosed herein To facilitate understanding, identical reference numerals have been used, wherever possible, to designate identical elements that are common to the figures.

FIG. 7 depicts a side view of a fifth integrated pull-up system 700 in accordance with aspects disclosed herein. The system 700 includes the gantry 112, the PHS 104, and the imaging bed 104. In addition, the system 700 includes a boom 702. In various embodiments, for support, one end of the boom 702 is mounted on an upper portion of a medical imaging device, at a base of the medical imaging device, integrated on the medical imaging device, or on the PHS 104. The other end of the boom 702 is coupled to a housing 704. The housing 704 includes a tube/rod 706. A longitudinal axis of the tube/rod 706 is substantially horizontal to the imaging bed 104 and substantially perpendicular to the end of the boom 702 coupled to the housing 704. Inside the housing 704 is a motor which rotates the tube/rod 706 clockwise or counterclockwise, as needed. Connected to one end of the tube/rod 706 is a cable/strap $708_1$ and connected to the other end of the tube/rod 706 is a cable/strap $708_2$ (cable/straps $708_1$ and $708_2$ are collectively referred to hereinafter as cable/straps 708). Coupled to the distal end (with respect to the tube/rod 706) of the cable/straps 708 are a grab bar 712 and a sling 710.

The grab bar 712 and the sling 710 are each adapted to couple directly to the distal ends of the cable/straps 708. In various embodiments, the grab bar 712 is adapted to couple to the sling 710 when the sling 710 is coupled directly to the distal ends of the cable/straps 708. In yet other embodiments, the sling 710 is adapted to couple to the grab bar 712 when the grab bar 712 is coupled directly to the distal ends of the cable/straps 708.

Although FIG. 7 depicts both the grab bar 712 and the sling 710 coupled to the cable/straps 708, it is appreciated that in accordance with aspects disclosed herein only one of the sling 710 and the grab bar 712 may be used.

A controller 714 actuates rotation of the tube/rod 706. As the tube/rod 706 rotates the cable/straps 708 either wrap/unwrap (depending upon the current position of the cable/straps 708) around the tube/rod 706. The length of the cable/straps 708 changes in accordance with the wrapping/unwrapping of the cable/straps 708 thereby moving a patient towards/from a supine position towards/from a seated position. For example, when actuation of the controller 714 causes rotation of the tube/rod 706 to wrap the cable/straps 708 around the tube/rod 706 the length of the cable/straps 708 shortens and moves a patient holding the grab bar 712 and/or cradled in the sling 712 to move towards an upright seated position.

Although, the controller 114 (depicted in FIGS. 1, 3, and 4) and the controller 714 (depicted in FIG. 7) are depicted as being mounted on the gantry 112 that depiction is not intended in any way to limit the scope of the invention. For example, in various embodiments, the controller 114 and the controller 714 are at least one foot pedal controlled by a technologist's foot (thereby freeing both of the technologist's hands). In yet other embodiments, the controller 114 and the controller 714 are integrated into the controller which controls the imaging system.

Although the sling 202 (depicted in FIGS. 2 and 3) and the sling 710 (depicted in FIG. 7) are depicted as slings which are positioned across a patient's back that depiction is not intended in any way to limit the placement and/or width of either sling 202 or sling 710. For example, in various embodiments, the size of the sling 202 and sling 710 is increased to support a patient's back, head, and/or neck. The enlarged sling may have a portion(s) contoured to support the neck and/or head to restrict movement (and limit discomfort and injury) to the head and/or neck.

While the foregoing is directed to embodiments of the present invention, other and further embodiments of the invention may be devised without departing from the basic scope thereof, and the scope thereof is determined by the claims that follow.

The invention claimed is:

1. An integrated pull-up system comprising:
    an electric hoist adapted for mounting on one of an upper portion of a medical imaging device and at a base of said medical imaging device, or integrated on said medical imaging device, a patient handling system ("PHS") wherein said PHS includes a substantially horizontal bed for accommodating a patient and wherein said bed is spaced from said electric hoist in a horizontal direction, wherein said electric hoist is substantially proximate to a foot end of said bed and substantially distal from a head end of said bed;
    a cable/strap having a first and second end wherein said first end is adapted for coupling to said electric hoist; and
    a grab-bar adapted for coupling to said second end of said cable/strap,
    wherein said grab-bar is configured to be grasped by said patient and said electric hoist causes movement of said cable/strap wherein said movement includes an approximately horizontal component toward said foot end of said bed to move said patient between sitting and supine positions on said bed.

2. The system of claim 1 wherein said upper portion is a gantry.

3. The system of claim 1 further comprising a sling coupled to said grab-bar,
    wherein said sling is adapted to support at least one of a head, a neck, and a back.

4. The system of claim 1 further comprising a controller to actuate said electric hoist,
    wherein said actuation retracts and extends said cable/strap.

5. The system of claim 1 further comprising a medical imaging controller adapted to control said electric hoist.

* * * * *